(12) United States Patent
Thind et al.

(10) Patent No.: US 12,121,654 B2
(45) Date of Patent: Oct. 22, 2024

(54) DEVICE AND METHOD FOR DETERMINING AN INFORMATION RELATING TO A TREATMENT

(71) Applicant: Linde GmbH, Pullach (DE)

(72) Inventors: Mandip Thind, Southall (GB); Brian Jacobsen, London (GB); Dennis Reid, Pulborough (GB)

(73) Assignee: LINDE GMBH, Pullach (DE)

( * ) Notice: Subject to any disclaimer, the term of this patent is extended or adjusted under 35 U.S.C. 154(b) by 705 days.

(21) Appl. No.: 17/309,689

(22) PCT Filed: Dec. 10, 2019

(86) PCT No.: PCT/EP2019/025443
§ 371 (c)(1),
(2) Date: Jun. 15, 2021

(87) PCT Pub. No.: WO2020/126080
PCT Pub. Date: Jun. 25, 2020

(65) Prior Publication Data
US 2022/0080139 A1    Mar. 17, 2022

(30) Foreign Application Priority Data
Dec. 19, 2018 (EP) ..................................... 18214193

(51) Int. Cl.
*A61M 16/00* (2006.01)
*A61B 5/00* (2006.01)
(Continued)

(52) U.S. Cl.
CPC ....... *A61M 16/0003* (2014.02); *A61B 5/0816* (2013.01); *A61B 5/091* (2013.01);
(Continued)

(58) Field of Classification Search
CPC .......... A61M 16/0003; A61M 16/0051; A61M 16/024; A61M 2016/0027;
(Continued)

(56) References Cited

U.S. PATENT DOCUMENTS

| 5,558,086 A | 9/1996 | Smith et al. |
| 2007/0181127 A1* | 8/2007 | Jin ........................ A61M 16/08 128/204.21 |

(Continued)

FOREIGN PATENT DOCUMENTS

EP    3127574 A1    2/2017

*Primary Examiner* — Andrey Shostak
(74) *Attorney, Agent, or Firm* — Millen, White, Zelano & Branigan P.C.; Brion P. Heaney

(57) ABSTRACT

The present invention pertains to a device and corresponding method for determining information relating to the treatment of a patient, preferably relating to a patient having a respiratory disorder. The device comprises a fluid channel configured to be in fluid communication with a medical gas source at a first end and with a patient interface at a second end, a sensor arrangement having at least a first sensor for measuring a value of a first flow parameter in the channel and a second sensor for measuring a value of a second flow parameter in the channel, wherein the first sensor and the second sensor are spaced apart from each other along a longitudinal axis of the channel, and a control unit in communication with the first sensor and the second sensor. The control unit determines flow direction of a medical gas in the channel based on sensor measurements.

10 Claims, 2 Drawing Sheets

(51) Int. Cl.
  *A61B 5/08* (2006.01)
  *A61B 5/091* (2006.01)
  *A61B 5/097* (2006.01)
(52) U.S. Cl.
  CPC ............ *A61B 5/097* (2013.01); *A61B 5/7275* (2013.01); *A61M 16/0051* (2013.01); *A61M 16/024* (2017.08); *A61M 2016/0027* (2013.01); *A61M 2016/0033* (2013.01); *A61M 2205/13* (2013.01); *A61M 2205/14* (2013.01); *A61M 2205/3334* (2013.01); *A61M 2205/3553* (2013.01); *A61M 2205/581* (2013.01); *A61M 2205/583* (2013.01); *A61M 2230/40* (2013.01)
(58) Field of Classification Search
  CPC ...... A61M 2016/0033; A61M 2205/13; A61M 2205/14; A61M 2205/3334; A61M 2205/3553; A61M 2205/581; A61M 2205/583; A61M 2230/40; A61M 2205/3584; A61M 2205/3592; A61M 16/0841; A61M 2016/0039; A61M 2205/18; A61M 2205/505; A61M 2205/587; A61B 5/0816; A61B 5/091; A61B 5/097; A61B 5/7275; A61B 5/4836; A61B 5/746; A61B 2560/0276; A61B 2562/0247; A61B 5/087; A61B 5/4833; A61B 5/0022
  See application file for complete search history.

(56) References Cited

U.S. PATENT DOCUMENTS

| | | |
|---|---|---|
| 2011/0259327 A1 | 10/2011 | Wondka et al. |
| 2015/0320949 A1 | 11/2015 | Jaffe |
| 2015/0320953 A1* | 11/2015 | Acker ................. A61M 16/202 128/203.14 |
| 2016/0256657 A1 | 9/2016 | Klasek et al. |
| 2021/0178110 A1* | 6/2021 | Barnes ................ A61M 16/209 |

* cited by examiner

DEVICE AND METHOD FOR DETERMINING AN INFORMATION RELATING TO A TREATMENT

TECHNICAL FIELD

The invention relates to a device for determining an information relating to a treatment of a patient, for example relating to an adherence of a patient having a respiratory disorder and in particular to a device for facilitating a correct measurement of such adherence. Furthermore, the invention relates to a corresponding method for determining an information relating to a treatment of a patient.

TECHNOLOGICAL BACKGROUND

Patients having a respiratory disorder or having an impaired respiratory function are often prescribed with a medical gas therapy. For example, patients with acute chronic obstructive pulmonary disease (COPD) are generally prescribed long term oxygen therapy (LTOT), which is preferably provided at a location remote from a medical facility, preferably at the patient's home. Such therapy can be provided from a number of medical gas sources including gaseous oxygen (GOX), liquid oxygen (LOX), or is provided by e.g. oxygen concentrators.

To ensure that a medical gas therapy is provided in an efficient manner and to ensure a best possible outcome, i.e. an improved effect on the physiological parameters of a patient treated with a medical gas, it is important that the medical gas is effectively applied according to a prescribed dosage regimen. This is particularly the case for patients requiring a prolonged medical gas application, which may be up to 16 hours per day for e.g. patients suffering from COPD. Accordingly, it is important that the adherence of a patient, i.e. the effective application according to a treatment prescription, is determined and improved to provide a maximum therapeutic outcome and to improve the patient's pathophysiological condition.

Since the therapy may provide a level of discomfort to a patient and the patient may furthermore not always be capable of applying the prescribed medical gas therapy, e.g. when consuming a meal, transiting between locations, or when performing personal hygiene, the adherence may be reduced. To determine the adherence, several adherence devices are known, which may e.g. monitor the medical gas consumption or usage of the patient. Such devices may be connected in-line with a medical gas source, e.g. a gas cylinder. Accordingly, the adherence may be determined to e.g. provide feedback to a patient, provide therapeutic modifications, and/or predict future medical gas requirements.

However, even when an adherence device is provided in connection with a therapeutic device, it often occurs that the adherence device needs to be disconnected when, for example, a new nasal prong or mask is required or if the patient wishes to switch between medical gas sources. In such cases it may occur that the adherence device is connected in the wrong orientation, such that the adherence device may not determine or wrongly determines the patient adherence. Accordingly, this leads to a loss of available compliance data that may be provided by the device, such that the medical staff is unable to determine if the patient has been using the therapy correctly.

Furthermore, the user or patient is generally not aware of the fact that the adherence device, e.g. associated with or integrated with a part of tubing for a medical gas application device, is connected in the wrong orientation, such that a correction does not occur. The lack of such indication hence results in the potential loss of available compliance data and may furthermore result in a decreased performance as a whole. In addition, the user or patient may find it cumbersome to handle a device requiring a particular orientation or sequence of steps to function appropriately, which may lead to a loss of motivation or a reduced general acceptance of such devices and may hence further increase the occurrence of a loss of adherence data.

From US 2016/256657 A1 a flexible tape heater in a patient conduit is known, which may be used to heat the flow of gas in the patient conduit that is delivered to the patient mask. The conduit is implemented in a fixed configuration. Temperature sensors may additionally be used to provide a differential flow sensing so as to indicate a breathing phase of the patient. By the same token, a differential pressure measurement between a respiration machine and a patient is disclosed in combination with a fixed arrangement in US 2015/320949 A1. Alternatively, an adapter being connectable with yet lacking any sensor is suggested. Such arrangement of a single sensor is furthermore known from U.S. Pat. No. 5,558,086.

A three-way expectoration device is furthermore known from EP 3 127 574 A1, wherein sensors may be connected to detect a breathing onset and interruption. Furthermore, an implementation of two sensors at one end of a device that is configured as a patient interface in the form of a ventilation tube is known from US 2011/259327 A1.

A method for judging the reverse connection of differential flow sensor is furthermore disclosed in US 2007/181127 A1, wherein a single differential pressure sensor is implemented to indicate a connection error and to output an alarm for correcting the erroneous connection.

SUMMARY OF THE INVENTION

Starting from the known prior art, it is an object of the present invention to provide a device and a method for determining an information relating to a treatment of a patient, which provide a facilitated coupling and parameter measurement.

Said object is achieved by a device and corresponding method for determining an information relating to an adherence of a patient having a respiratory disorder, according to the features of the independent claims. Preferred embodiments are defined in the dependent claims, the Figures, as well as the present description.

Accordingly, a device for determining an information relating to a treatment of a patient is suggested, which comprises a fluid channel configured to be in fluid communication with a medical gas source at a first end and with a patient interface at a second end, a sensor arrangement having at least a first sensor for measuring a value of a first flow parameter in said channel and a second sensor for measuring a value of a second flow parameter in said channel, wherein the first sensor and the second sensor are spaced apart from each other along a longitudinal axis of the channel, and a control unit in communication with the first sensor and the second sensor. The control unit is configured to determine a flow direction of a medical gas in the channel based on a received measurement of the first sensor and/or second sensor and to determine the information based on the determined flow direction.

The device may be any device that may be coupled between a patient interface and a medical gas source. For example, the device may be coupled to or integrated in a tube connecting a medical gas source to a patient interface or may be integrated, at least in part, in other components of a medical gas therapeutic system, e.g. in a pressure regulator configured to provide a predefined gas flow to a patient from a medical gas source or a monitoring unit. The device hence comprises a fluid channel, which provides a fluid connection between a medical gas source and a patient interface and preferably extends linearly along a longitudinal axis of said device. The channel may furthermore be configured to direct any fluid and is preferably configured to direct a gas flow from one end to the other end of the device. The channel may e.g. be provided in the form of a tube, a tube section, line, or conduit, preferably a medical grade flexible tube, but may also be defined by a cavity in the device. Preferably, the channel is dimensioned to enable a medical gas application in the range o at least 0.1 to 20 liters per minute.

Furthermore, the sensor arrangement at least comprises a first and a second sensor, which are spaced apart from each other along a longitudinal axis of the device. For example, a first one of the sensors may be arranged in proximity of or at a first end of the device or channel while a second sensor may be arranged e.g. at a central position of the channel or at a respective other end of the channel. The sensors preferably are connected symmetrically via e.g. two accordingly dimensioned chambers which are used to increase the sensitivity of the measurement.

The spacing between the first and second sensors along a longitudinal axis of the device is to be understood as a spacing in a direction of a fluid flow in the fluid channel rather than a radial spacing with regard to the fluid channel. In other words, the spacing may relate to a downstream and corresponding upstream arrangement of said sensors, which may essentially correspond to a longitudinal axis of the device, e.g. in the case of a tube. Depending on the geometry of the fluid channel and/or the device said sensors hence do not need to be spaced apart in a uniaxial manner, but may also be arranged e.g. in a curvature, such as at an end of a bent tube. Furthermore, the arrangement may optionally also comprise a radial spacing or circumferential spacing along a wall of the fluid channel.

The flow parameter to be measured may be e.g. a pressure, a flow speed, and/or flow volume. Accordingly, by means of a corresponding coupling or integrated configuration of the device, as described in the above, a flow parameter of a medical gas being delivered to a patient interface to apply the medical gas to said patient may be measured.

The sensor arrangement is connected to a control unit, which may be configured to process the received measurement values from the respective sensors. The control unit may e.g. be configured as a processor or microprocessor or any other control circuitry and preferably comprises a control logic, e.g. in the form of lists, protocols, and/or algorithms to determine the flow direction and determine and/or indicate the information from the received measurement values.

The information relating to a treatment of a patient preferably relates to an adherence of a patient, preferably an adherence of a patient having a respiratory disorder. For example, the patient to be treated with a medical gas may e.g. suffer from COPD, cystic fibrosis, or a pulmonary infection, wherein the adherence is a measure for the compliance of a patient to a prescribed medical treatment, e.g. a type and dosage regimen of a medical gas. Such adherence data may hence be provided by the device by simply determining an onset of a measurement to indicate that a treatment is started. However, it may occur that the device is not properly connected, such that more particular adherence data, e.g. the flow rate of the medical gas in the channel of the device or the applied volume of the medical gas over time, may not be determined due to invalid measurements. Accordingly, the flow direction may be used to indicate whether valid adherence measurements may be obtained or not.

Although the device is of particular relevance for patients having respiratory disorders, the device may also be applied for medical gas applications for patients suffering from other diseases. For example, patients suffering from cardiovascular disorders or heart diseases may require an increased oxygen respiration and intake while in general patients may be provided with gaseous analgesic agents for a variety of diseases, dysfunctions, disorders, and/or treatments.

Accordingly, the information may provide feedback as to the actually applied medical gas, such that prescriptions and treatments may e.g. be accordingly adapted.

In order to determine the flow direction, the first sensor and the second sensor of the device may be configured to measure the same flow parameter, wherein the control unit is configured to calculate a differential pressure calculated from the measurements of the first sensor and the second sensor. Alternatively, one of the sensors may be configured as a differential pressure sensor to measure a differential pressure. Accordingly, the control unit may then determine the flow direction based on the determined differential pressure.

For example, the first sensor and the second sensor of the device may be arranged at opposite ends of the channel and may be configured to measure a pressure. The control unit may then determine a virtual differential pressure measurement by creating an artificial impedance in the channel between the first sensor and the second sensor, wherein the exact positions of the sensors and the characteristics of the channel are preferably known. In a connected or coupled state, i.e. in a system with a medical gas source and a patient interface, the pressure measured at the sensor located nearest to the medical gas source, e.g. at a gas inlet, will be higher than the measured pressure at the other sensor, e.g. at a gas outlet or a gas inlet of a patient interface, such that a flow direction may be determined based on the calculated differential pressure and/or the respective pressure at each of the sensors.

Furthermore, the flow direction may be determined e.g. by providing a time or frequency synchronization of the measurement values for both sensors, such that a deviation or fluctuation of said measurement values may indicate the flow direction in the channel.

Alternatively, or in addition, a differential pressure sensor may be provided in the sensor arrangement, which measures a pressure difference at two sides of the sensor. The differential pressure sensor may be arranged at a respective end of the channel, but may also be arranged at a central position thereof. Accordingly, the differential pressure provides either a negative or a positive measurement value depending on the flow direction with respect to the differential pressure sensor. Accordingly, the control unit may directly determine the flow direction based on said measurement value.

The determined information may furthermore indicate a coupling orientation of the device, wherein the device may be configured to output a signal based on the determined information. For example, by determining the flow direction within the channel and by knowing the relative positions of the sensors, the orientation of the channel and hence the device between a medical gas source and a patient interface may be determined. Accordingly, the device may detect how the device is coupled to the respective components of a treatment system.

Preferably, the output signal is a visual and/or acoustic alarm or alert. For example, when the sensor arrangement of the device is configured such that patient relevant flow characteristics may only be measured in a particular flow direction, the determined coupling orientation of the device may hence indicate a correct or incorrect coupling. In case of an incorrect coupling orientation, the device may hence output e.g. an acoustic alarm, e.g. via a buzzer or speaker, and/or visual indication, e.g. by a lighting device or LED. By the same token, a correct coupling may also be indicated by a corresponding different acoustic alarm or visual indication.

Accordingly, the patient or user may be provided with a feedback after the coupling of the device and may hence be pointed to an incorrect coupling. Thereby, a user may be directly or indirectly prompted to check the current coupling and may be required to reverse the orientation of the device in order to allow a proper measurement of the information, e.g. the adherence. Furthermore, the correct coupling may provide e.g. predefined flow characteristics, such that a proper arrangement of the device may provide an improved performance of the device and e.g. a medical gas application as a whole. The occurrence of a mismatch or wrong assembly or coupling is hence significantly reduced, thereby increasing the availability of measured or determined information, e.g. reliable adherence data.

To output the signal on the device the device preferably comprises a signaling device. Alternatively, or in addition, the device may comprise a communication device to communicate the signal to an external and/or coupled device to output said signal. A signaling device provided on the device preferably comprises a display, such that a patient or user may be provided with a visual feedback regarding the orientation of the device. The display may e.g. be any screen or monitor, e.g. a touch screen, to indicate the coupling and/or an action to be accordingly performed. The direct, visual feedback has the advantage that the user or patient may be immediately assisted in the correct coupling and is assured that the coupling is performed correctly, thereby reducing the stress level for the patient while at the same time ensuring that e.g. adherence data and or other information may be measured, collected, and obtained.

The communication device may furthermore be provided to communicate the determined information to an external or remote device. For example, the communication device may be coupled via buses or links to other components of the system to communicate said information or may be configured to transmit said information to a remote device. For example, the communication device may be configured for wireless transmission, e.g. via Bluetooth, Bluetooth Low Energy (BLE), Zigbee, RFID, near-field communication (NFC), WAN, WLAN, infrared signaling, and/or any other broadcasting means.

The provision of such a communication device has the advantage that medical personnel may be accordingly informed and undertake an action, if required. For example, medical personnel may contact the patient, when a situation persists, wherein the coupling is incorrect and/or wherein the information may not be determined. Furthermore, if the coupling orientation is correct, the determined information may be accordingly examined, such that a treatment may be modified or maintained, if required.

Preferably, the device is configured such that either end of the channel is configured to be coupled to a medical gas source or a patient interface. Accordingly, the couplings on either end may be configured symmetrically or at least comprise a corresponding mechanism, such as e.g. a Luer-Lock interface.

This has the advantage that the user or patient may couple the device to a treatment system, e.g. to an outlet of a medical gas source and/or to an inlet of a patient interface, in any orientation, such that the device may operate, with respect to the sensor arrangement, in any flow orientation, e.g. also with inlet and outlet ports in a reversed orientation. This significantly facilitates the coupling of the device as a potential mismatch or wrong coupling is avoided. By means of the known sensor arrangement and configuration, the control unit then ensures that a measurement of a flow characteristic may be performed based on the determined flow direction. For example, the control unit may determine the flow direction and/or coupling orientation as described in the above and may select a particular sensor, depending on the relative position and e.g. the flow direction, to perform a measurement of a flow characteristic at a downstream end of the channel.

In other words, the facilitated coupling provides an omni-directional device, which is compatible with both orientations and may hence allow a measurement in both flow directions. The considerations and necessary cognitive steps for a user or patient to assemble the device to perform e.g. a medical gas application may hence be significantly reduced and at the same time the availability of e.g. reliable adherence data is significantly increased.

The device hence allows for a more accurate determination of the information, e.g. the patient adherence, since the device provides an alert when it is incorrectly connected and/or it is purposely configured such that e.g. the inlet/outlet tubing of system components to be coupled with can be connected to either end of the device. In this case, the installation time may be reduced and also leads to less chance of installation error.

In order to provide further patient-related information, at least one of the sensors is preferably configured as a flow sensor or pressure sensor, wherein the at least one flow sensor is configured to measure a respiratory parameter of the patient based on the determined flow direction and the measurement value of the at least one flow sensor or pressure sensor. The control unit may be configured to then determine the information based on the measured respiratory parameter.

Such configuration has the advantage that the flow variation in the line due to patient respiration may be measured. For example, a pressure sensor at a downstream end of the channel may be arranged to detect the patient respiration and measure a flow characteristic, e.g. a pressure or flow rate. Furthermore, the sensor arrangement may comprise multiple sensors, wherein a corresponding sensor is e.g. arranged at a respective other end of the channel. By means of determining the flow direction, the control unit may then select the downstream sensor to measure the respiratory parameter. Accordingly, the determined information may provide more details regarding the adherence and/or the respiratory behavior of the patient being treated with a medical gas.

In addition, the device may furthermore comprise an evaluation unit in communication with the control unit, wherein the evaluation unit is configured to determine a physiological parameter of the patient based on the measured respiratory parameter of the patient. The control unit may then determine the information based on the determined physiological parameter of the patient.

For example, the physiological parameter may comprise e.g. a determined oxygen respiration, blood oxygenation level, and/or a respiratory function based on a determined respiratory parameter.

Preferably, the information comprises an exacerbation prediction of the patient. For example, based on the measured respiratory parameter and the determined physiological parameter, the evaluation unit may indicate a course or progression of a patient condition and may detect a trend in said condition to indicate a probability of a potentially upcoming exacerbation, i.e. a worsening of a patient's disease status or worsening of the patient's condition.

To determine the physiological parameter the evaluation unit is furthermore preferably configured to evaluate the measured respiratory parameter comprising a breathing pattern or rhythm, an exhalation and/or inhalation time, a breathing volume, a dynamic flow measurement, a breathing or maximal lung capacity, and/or a breathing pulse, preferably over a predefined time and/or at predefined intervals.

Accordingly, various characteristics may be determined and e.g. a change of said characteristics detected by the evaluation unit may provide a trend or course of the patient's physiological parameter. Furthermore, the evaluation of the parameter may include an averaging, such that measuring values that occur infrequently and may be considered as outliers do not immediately alter the determined patient's physiological parameter.

The device hence provides a more reliable and higher quality data collection from the device, thereby allowing better capturing of e.g. adherence data and, where the data or information from the device is used in exacerbation prediction, there exists the potential for greater accuracy in determining potential exacerbation conditions.

Preferably, the evaluation unit is furthermore configured to determine the flow rate and/or the flow volume of a medical gas and/or a change thereof provided in the channel, preferably over a predefined time and/or at predefined intervals, wherein the control unit determines the information based on the determined flow rate and/or the flow volume of the medical gas.

For example, when multiple pressure sensors are provided in the sensor arrangement, e.g. when two pressure sensors or flow sensors are arranged at opposite ends of the channel, respectively, the control unit may measure both a respiratory parameter, i.e. at a downstream end of the channel, and a flow characteristic of the medical gas provided in the channel, e.g. at an upstream end of the channel or at a position upstream of the sensor measuring the respiratory parameter. Accordingly, more detailed information may be determined relating to both the medical gas being applied and the corresponding respiratory function of the patient being treated.

The device may furthermore comprise a monitoring unit in communication with the control unit, wherein the monitoring unit is configured to compare the determined information, the measured respiratory parameter, and/or the determined physiological parameter with a corresponding threshold or control logic stored in the monitoring unit and is configured to automatically output a signal, when said threshold is exceeded and/or based on a value of said control logic.

Providing a monitoring unit hence has the advantage that a patient condition may be monitored over time and potential safety hazards may be avoided, e.g. when a determined physiological parameter indicates an exacerbation. In such case, the control unit may output an alarm, either on the device or by transmitting a corresponding signal to e.g. a remote location, as outlined in the above. By the same token, the monitoring unit may detect that a medical gas flow or pressure in the system e.g. exceeds tolerable levels and hence may be harmful for a patient having a limited respiratory function. To avoid a potential excess pressure, the monitoring unit may provide an alarm and/or display a corresponding signal on e.g. the device directly to warn a patient.

Accordingly, the monitoring unit increases the safety of the patient. Such monitoring unit may be comprised in the device or may be coupled to the device as an external monitoring unit. Furthermore, the device may also be configured as a component of a monitoring unit, e.g. as a monitoring device or system. The monitoring unit may be either provided with the measured or determined parameter or information by the control unit or may be in communication with an evaluation unit directly.

To ensure that the determined information, the measured respiratory parameter of the patient, and/or the determined physiological parameter may be retrieved and accessed at any time point, the evaluation unit is preferably configured to store the determined information, the measured respiratory parameter of the patient, and/or the determined physiological parameter of the patient in a database of the device. Alternatively, or in addition, the device comprises a communication device to communicate the determined information, the measured respiratory parameter of the patient, and/or the determined physiological parameter of the patient to an external database for remote storage.

Hence, the patient relevant information may be stored locally and/or externally. While a local storage may provide a direct access at the device, an external storage has the advantage that the relevant information may be accessed from one or more remote locations to provide e.g. an improved monitoring of the patient. Furthermore, an external storage may provide that a more advanced analysis be performed using a plurality of data entries and/or a comparison of data entries while at the same time the device may be dimensioned more compact. This may be particularly advantageous when the device and the corresponding treatment system are configured as a portable system.

Furthermore, the control unit may be configured to be in communication with a pressure regulator of the medical gas source and/or of the patient interface to automatically adjust the medical gas flow based on the determined information and/or on a comparison of the determined information with a prescribed treatment of the patient provided in the control unit.

For example, a patient may be prescribed with a medical gas flow rate in the range of e.g. 1 to 15 liters per minute, wherein said medical gas may be provided either continuously or may be delivered on demand, e.g. via a demand valve or an oxygen concentrator which itself delivers an equivalent flow in a series of pulses. Based on the above comparison, the control unit may hence actuate the pressure regulator according to the provided prescribed treatment.

Accordingly, should the control unit determine an information, e.g. a reduced or changed value of a measured respiratory parameter or an exacerbation, the control unit may accordingly regulate or increase the medical gas flow to remedy said detected reduction or change. By the same token, the control unit may automatically stop a treatment, e.g. when one of the sensors measures a pressure that exceeds a pressure limit or when a prescribed treatment is completed or to be paused.

By the same token, the control unit may furthermore be configured to be in communication with a remote control device to control the pressure regulator based on the determined information. For example, the device may comprise a communication device to communicate the determined information to a remote control device, i.e. an external device, such that a user or medical personnel may accordingly adjust the medical gas application by actuating e.g. the pressure regulator via the control unit of the device. Accordingly, a further control level is provided to further increase the safety and the application of the medical gas to a patient.

According to a further aspect of the invention, a method for determining an information relating to a treatment of a patient is suggested, preferably relating to an adherence of a patient having a respiratory disorder, comprising the steps of:
measuring a value of a first flow parameter in a fluid channel configured to be in fluid communication with a medical gas source at a first end and with a patient interface at a second end using a first sensor of a sensor arrangement;
measuring a value of a second flow parameter in said channel using a second sensor of said sensor arrangement at a position spaced apart from the first sensor along a longitudinal axis of the channel;
determining a flow direction of a medical gas in the channel using a control unit based on the measured first flow parameter and second flow parameter communicated to said control unit; and
determining the information using the control unit based on the determined flow direction.

Said method may be performed by the device as described in the above. Accordingly, various features and other functions of the described device may be provided in accordance with the suggested method, which are not described in further detail for redundancy reasons.

Furthermore, the method may comprise the steps of:
calculating a differential pressure from the measurements of the first sensor and the second sensor, wherein the first flow parameter and the second flow parameter are the same, or measuring a differential pressure, wherein one of the sensors is configured as a differential pressure sensor; and
determining the flow direction based on the determined differential pressure.

Preferably, the determined information indicates a coupling orientation of the device and a signal is preferably outputted based on the determined information, preferably a visual and/or an acoustic alarm.

Accordingly, a patient or user may be provided with a direct feedback regarding the orientation of the device, e.g. by indicating the orientation and/or an action to be accordingly performed on a display. The direct, visual feedback has the advantage that the user or patient may be immediately assisted in the correct coupling and is assured that the coupling is performed correctly, thereby reducing the stress level for the patient while at the same time ensuring that e.g. adherence data and or other information may be measured, collected, and obtained.

BRIEF DESCRIPTION OF THE DRAWINGS

The present disclosure and preferred embodiments will be more readily appreciated by reference to the following detailed description when being considered in connection with the accompanying drawings in which.

DETAILED DESCRIPTION OF PREFERRED EMBODIMENTS

Figure 1:
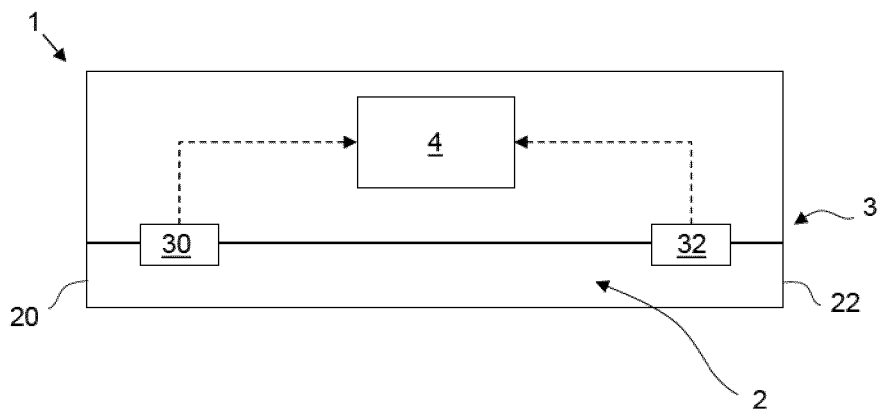
FIG. 1 is a schematic view of a device for determining an information related to a patient treatment with a sensor arrangement with a first and second sensor.

In the following, the invention will be explained in more detail with reference to the accompanying figures. In the Figures, like elements are denoted by identical reference numerals and repeated description thereof may be omitted in order to avoid redundancies.

In FIG. 1 a device 1 for determining an information related to a patient treatment is schematically shown. Accordingly, the device 1 comprises a fluid channel 2, which extends along a longitudinal axis of the device and comprises a first end 20 and a second end 22, which may be coupled to corresponding connectors of a medical gas source and a patient interface, respectively. The channel 2 is configured and dimensioned to allow a medical gas to pass through the channel 2 from one end 20, 22 to a respective opposing end 22, 20, such that a minimal resistance is provided and a medical gas may be applied to a patient according to a prescribed dosage regimen.

Furthermore, a first sensor 30 and a second sensor 32 are arranged along the channel 2 and at respective ends 20, 22 of said channel. The first sensor 30 and the second sensor 32 are in fluid communication with the channel 2 and are configured to measure a flow parameter of a medical gas provided in said channel 2. Although the sensors 30, 32 of the sensor arrangement 3 may have various configurations, the first sensor 30 and the second sensor 32 according to the exemplary embodiment of FIG. 1 are configured as pressure sensors.

In addition, it is to be understood that the schematic depiction is merely provided by means of an example. For example, the sensors 30, 32 are depicted in an essentially symmetrical arrangement along a longitudinal axis of the device 1. However, the spacing between the first and second sensors 30, 32 may also be asymmetrical, such that at least one of the sensors 30, 32 may be arranged at a further or closer distance to the respective end 20, 22. In addition, the spacing along a longitudinal axis of the device is merely optional and is generally to be understood as a spacing in a direction of a fluid flow in the fluid channel 2 rather than a radial spacing with regard to the fluid channel 2.

In other words, the spacing may relate to a downstream and corresponding upstream arrangement of said sensors 30, 32, which may essentially correspond to a longitudinal axis of the device 1, as is the case in the embodiment shown in the schematic depiction of FIG. 1. Depending on the geometry of the fluid channel 2 and/or the device 1 said sensors 30, 32 hence do not need to be spaced apart in a uniaxial manner, but may optionally also be arranged e.g. in a curvature, such as at an end of a bent tube. Furthermore, the arrangement of the sensors 30, 32 may optionally also comprise a radial spacing or circumferential spacing along a wall of the fluid channel 2. Hence, a variety of sensor arrangements 3 is provided.

Both the first sensor 30 and the second sensor 32 are in communication with a control unit 4 provided in the device 1. The control unit 4 is hence configured to receive a measurement value of a measured pressure of a medical gas in the channel 2 from the first sensor 30 and the second sensor 32.

Since the first sensor 30 and the second sensor 32 of the device 1 are arranged at opposite ends 20, 22 of the channel 2, the sensors 30, 32 may be either in proximity of a medical gas source or a patient interface in a coupled state. Since the control unit 4 is provided with measurement values from each sensor 30, 32, it is required that the control unit 4 is capable of associating the respective measurement value with either an input measurement, i.e. a medical gas flow provided via e.g. a pressure regulator of a medical gas source, or an output measurement, i.e. a medical gas flow provided at a patient interface.

In order to facilitate such association, the control unit 4 calculates a virtual differential measurement by creating an artificial impedance in the channel 2 between the first sensor 30 and the second sensor 32, wherein the exact positions of the sensors 30, 32 and the characteristics of the channel are known. In a connected or coupled state, i.e. in a system with a medical gas source and a patient interface, the pressure measured at the sensor located nearest to the medical gas source, e.g. at a gas inlet, will be higher than the measured pressure at the other sensor, e.g. at a gas outlet, such that a flow direction may be determined based on the calculated differential pressure and/or the respective pressure at each of the sensors. Accordingly, the control unit 4 determines the flow direction based on a calculated differential pressure.

Based on said flow direction, the control unit 4 may then determine the information, which may e.g. indicate whether the device 1 is connected in the correct orientation. Said information may either be stored, e.g. for a later analysis and evaluation indicating that e.g. no adherence data could be determined for a specific time period, or may be used or retrieved directly.

Figure 2:
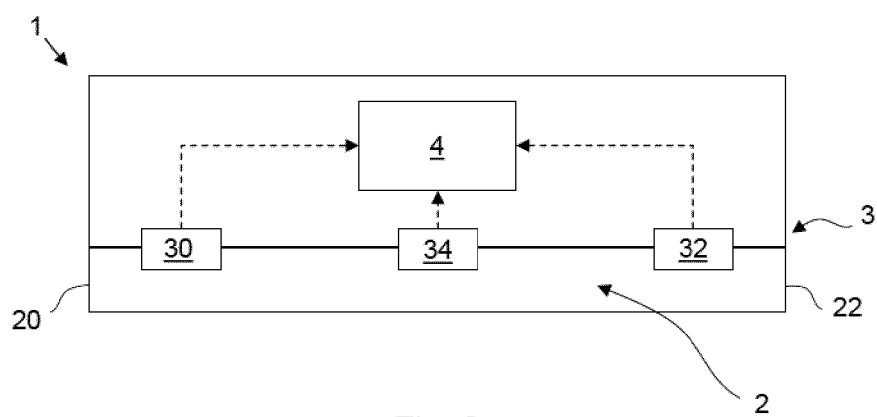
FIG. 2 is a schematic view of a device for determining an information related to a patient treatment with a sensor arrangement with a first and second sensor according to FIG. 1 with a differential pressure sensor.

An alternative determining of the flow direction is shown in the embodiment according to FIG. 2. Accordingly, again, the device 1 comprises the fluid channel 2 and the sensor arrangement 3, which is in communication with the control unit 4. In addition, a differential pressure sensor 34 is provided, which is arranged at the channel 2 along the longitudinal axis of the device 1 and between the first sensor 30 and second sensor 32.

The differential pressure sensor 34 comprises a membrane which represents a pneumatic impedance to the flow of gas in the channel 2. Accordingly, the differential pressure sensor 34 directly measures a pressure difference at two sides of the sensor 34 and accordingly provides a differential pressure having either a negative or a positive measurement value, depending on the flow direction with respect to the differential pressure sensor 34. The control unit 4 may then directly determine the flow direction based on said measurement value.

By means of the differential pressure sensor 34 the flow direction may be immediately determined and a calculation or comparison of measurement values of the first sensor 30 and the second sensor 32 is not required. Although the differential pressure sensor 34 is depicted to be arranged at a central position of the channel 2, the sensor 34 may also be arranged at a respective end 20, 22 of the channel 2. Accordingly, the device 1 may also be configured to comprise only one sensor 30, 32 configured to measure a flow characteristic at a respective other end 20, 22 of the channel 2.

Figure 3:
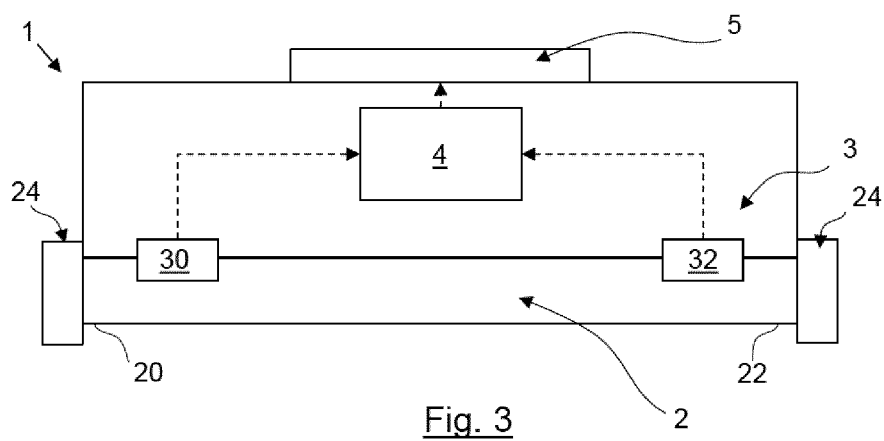
FIG. 3 is a schematic view of a device for determining an information related to a patient treatment with a sensor arrangement with a first and second sensor according to FIG. 1 with a signaling device and identical couplings.

Furthermore, the device 1 may not be compatible to measure a flow characteristic when the device 1 is not connected according to a predefined or desired orientation. To hence provide an alert to a user or patient, a corresponding signal may be provided via a signaling device 5, as shown in FIG. 3. The signaling device 5 is depicted as a display to visually indicate the orientation of the device 1. Accordingly, the patient is immediately provided with a feedback relating to the coupling of the device 1 to a corresponding medical gas source and/or patient interface.

In addition, the ends 20, 22 of the channel 2 are configured as identical couplings 24, such that the device 1 may be connected in either orientation. In other words, the outer industrial design is omnidirectional, i.e. it is intended that the user can connect the device 1 to the components of a treatment system, e.g. a gas output line of a medical gas source or pressure regulator, in any orientation.

As described in the above in view of FIG. 1, the control unit 4 determines the flow direction based on a calculated or virtual differential pressure and may then determine the information based on said flow direction. In particular, the information may furthermore comprise a measurement value provided by the respective sensors 30, 32, which may indicate the medical gas flow applied to the patient from the sensor at the upstream end, i.e. as seen from the determined flow direction in the channel 2, and e.g. a patient response to said gas flow by the measurement value of the sensor at the corresponding downstream end of the channel 2.

Such patient response may e.g. be provided as a measurement of a respiratory parameter, e.g. a breathing pattern or breathing variation, in particular, when the patient interface is provided with an on-demand valve and/or is configured as a nasal or face mask. By the same token, the measurement of the medical gas flow in the channel 2 may be used to measure the variation of flow caused by e.g. pressure regulator adjustments and/or a change of flow in the channel 2 caused by the respiratory effect of the patient. Accordingly, the information relating to the patient treatment may provide detailed information regarding the patient adherence.

Said information may be output in the signal provided at the display on the device, such that the patient or medical personnel not only is provided with a connection or coupling feedback but may also follow e.g. an adherence status. By the same token, this may provide a feedback as to a predefined target, e.g. a predefined time for the medical gas to be applied, which may be indicated with a corresponding timer on said display.

Figure 4:
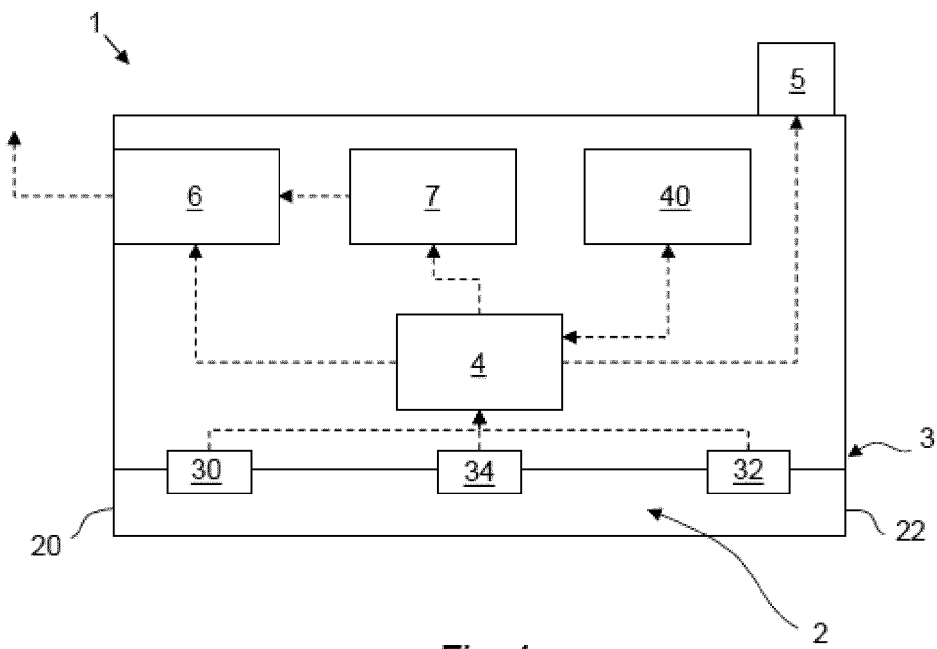
FIG. 4 is a schematic view of a device for determining an information related to a patient treatment with an evaluation unit and monitoring unit.

To provide even further information and a more detailed analysis of the measured or determined parameters, the device 1 may optionally comprise an evaluation unit 40 and/or a monitoring unit 7, as schematically shown in FIG. 4.

The evaluation unit 40 is in communication with the control unit 4 to receive the measurement parameters and/or the determined information from the control unit 4. From said received measurement values or data, the evaluation unit 40 is configured to determine a physiological parameter of the patient based on the measured respiratory parameter of the patient, such that the hence provided information may e.g. provide an exacerbation prediction of the patient.

Said prediction may e.g. be based on a breathing pattern or rhythm, an exhalation and/or inhalation time, a breathing volume, and/or a dynamic flow measurement, as measured by the sensor arranged at a downstream end of the fluid channel 2 determined by the differential pressure sensor 34. By the same token, a measurement from the sensor arranged at the corresponding opposite end of the channel may provide further information relating to the determined flow rate and/or the flow volume of the medical gas in the channel 2 and applied to the patient.

The control unit 4 and/or the evaluation unit 40 may be configured as e.g. a microcontroller or processor in the device 1 and may each comprise control logic to determine the information based on the received measurement values. Furthermore, although the control unit 4 and the evaluation unit 40 are depicted as separate components, they may also be combined in an integrated unit or device, which is either included in the device 1 or is arranged outside of the device 1 and communicates with the sensor arrangement 3 via a corresponding connection.

The device 1 furthermore comprises a monitoring unit 7, which is in communication with the control unit 4 and is configured to compare the determined information, the measured respiratory parameter, and/or the determined physiological parameter with a corresponding threshold or control logic stored in the monitoring unit 7. For example, the monitoring unit 7 may detect when a predefined threshold of a measured or determined parameter is exceeded by comparing the values with a corresponding list of values.

Furthermore, the monitoring unit 7 may be used to simply detect whether the device 1 is connected or coupled in the correct orientation or direction based on an output of the differential pressure sensor 34, i.e. by detecting whether the detected differential pressure is positive or negative.

Accordingly, the monitoring unit 7, which may also be integrated or combined with the evaluation unit 40 and/or the control unit 4, may provide either a feedback relating to the orientation of the device 1 and/or may provide detailed information relating to the patient treatment. In either case, the device may output a signal or alert via a signaling device 5, which is here depicted as an alarm generating unit or acoustic device. However, the signaling device may also be configured to output a visual alert, e.g. in the form of an LED.

In addition, the device 1 comprises a communication device 6, which enables a communication between the device 1 and an external device (not shown). Accordingly, the communication device 6 may communicate a signal or information provided by or via the control unit 4, as indicated by the dashed arrow. For example, should the evaluation unit 40 determine e.g. an adherence information or other information of the patient and/or the monitoring unit 7 detects that a device parameter, e.g. a pressure in the channel 2, is exceeded beyond tolerable levels, the control unit 4 may provide an information and/or alarm signal to an external device, e.g. a remote screen, a mobile device, or computer. Accordingly, medical personnel may perform an assessment of said information and/or alarm signal and may accordingly assess the treatment course and/or intervene, if necessary.

The information that is communicated via the communication device 6 may also be transmitted to be accordingly stored in an external database or cloud, such that the information may be retrieved at any other time point and at a remote location. As such, a data entry history may be provided, which facilitates a more detailed assessment of the treatment course of the patient, e.g. to accordingly provide modifications.

Figure 5:
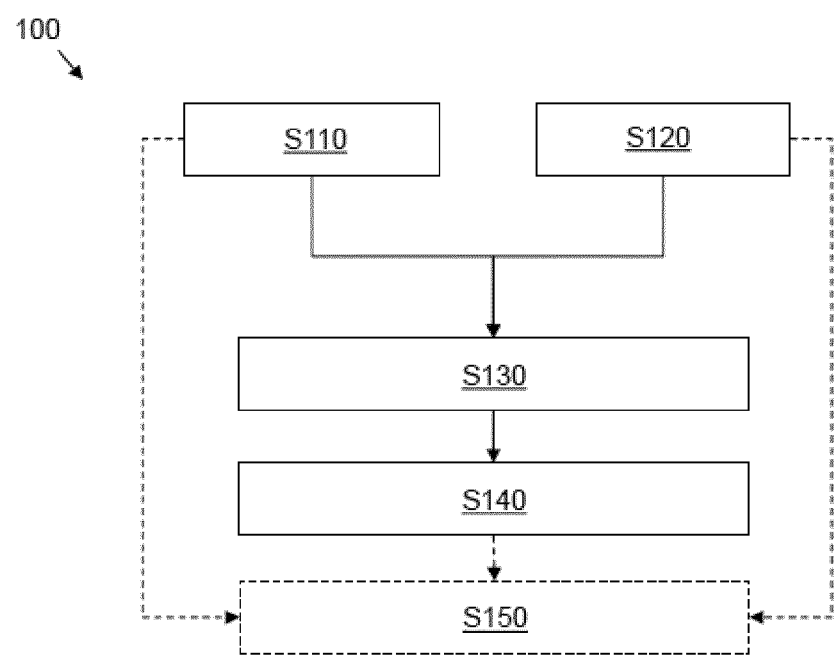
FIG. 5 is a method for determining an information related to a patient treatment.

FIG. 5 schematically shows a corresponding method 100 for determining an information related to a patient treatment. Said method 100 may e.g. be performed by the device 1 as described in the above, such that the method may comprise various other features and other functions. The method 100 comprises the step of measuring a value of a first flow parameter (S110) in a fluid channel configured to be in fluid communication with a medical gas source at a first end and with a patient interface at a second end using a first sensor of a sensor arrangement and measuring a value of a second flow parameter (S120) in said channel using a second sensor of said sensor arrangement at a position spaced apart from the first sensor along a longitudinal axis of the channel.

The channel may be any fluid channel that allows a fluid communication between either end of the channel, such that the channel may be coupled to a system for applying a medical gas to a patient without significantly reducing a gas flow or providing an additional resistance for said gas flow. Preferably, the measurements are performed within a connecting line or tube coupled between the medical gas source and a patient interface.

Based on the measured value of the first flow parameter and the second flow parameter, the method 100 then determines a flow direction of a medical gas in the channel using a control unit (S130). As described in the above, the flow direction may e.g. be determined by a differential pressure measurement performed by a differential pressure sensor or by measuring both measurement values measured by the sensors, e.g. configured as pressure sensors, and calculating a virtual differential pressure between said sensors. Based on the determined differential pressure the control unit may then determine the flow direction of the device.

From said determined flow direction, the information is then determined in a further step (S140). Accordingly, the method may provide that an information is determined indicating that no adherence data may be determined, e.g. when the device is not connected properly and/or no predefined gas flow is detected. Preferably, the determined information indicates whether the device 1 is connected in the correct orientation (S150). Said information may either be stored, e.g. for a later analysis and evaluation indicating that e.g. no adherence data could be determined for a specific time period, or may be used or retrieved directly, e.g. to output a corresponding signal.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

LIST OF REFERENCE NUMERALS

1 Device for determining an information
100 Method for determining an information
2 Fluid channel
20 First end
22 Second end
24 Coupling
3 Sensor arrangement
30 First sensor
32 Second sensor
34 Differential pressure sensor
4 Control unit
40 Evaluation unit
5 Signaling device
6 Communication device
7 Monitoring unit
S110 Measuring a value of a first flow parameter
S120 Measuring a value of a second flow parameter
S130 Determining a flow direction
S140 Determining the information
S150 Indicating a coupling orientation of the device

The invention claimed is:

1. A device for determining information relating to an adherence of a patient having a respiratory disorder, comprising:
   a fluid channel configured to be in fluid communication with a medical gas source at a first end and with a patient interface at a second end,
   a sensor arrangement having at least a first sensor for measuring a value of a first flow parameter in said channel and a second sensor for measuring a value of a second flow parameter in said channel, and
   a control unit in communication with the first sensor and the second sensor, wherein the control unit is configured to determine a flow direction of a medical gas in the channel based on a received measurement of the first sensor and/or second sensor and to determine the information based on the determined flow direction, wherein the first sensor and the second sensor are spaced apart from each other along a longitudinal axis of the channel and are arranged at opposing ends of the channel, wherein the device is configured such that either end of the channel is configured to be coupled to the medical gas source or the patient interface, wherein the determined information indicates a coupling orientation of the device and wherein the control unit is configured to select a particular sensor based on the coupling orientation and the relative position of the particular sensor to perform a measurement of a flow characteristic at a downstream end of the channel.

2. The device according to claim 1, wherein the first sensor and the second sensor are configured to measure the same flow parameter and wherein the control unit is configured to calculate a differential pressure calculated from the measurements of the first sensor and the second sensor, or wherein one of the sensors is configured as a differential pressure sensor to measure a differential pressure, wherein the control unit determines the flow direction based on the determined differential pressure.

3. The device according to claim 1, wherein the device is configured to output a visual and/or an acoustic alarm based on the determined information.

4. The device according to claim 1, wherein at least one of the sensors is configured as a flow sensor or pressure sensor, wherein at least one flow sensor is configured to measure a respiratory parameter of the patient based on the determined flow direction and the measurement value of the at least one flow sensor or pressure sensor, wherein the control unit is configured to determine the information based on the measured respiratory parameter.

5. The device according to claim 4, wherein the device furthermore comprises an evaluation unit in communication with the control unit, wherein the evaluation unit is configured to determine a physiological parameter of the patient based on the measured respiratory parameter of the patient, wherein the control unit determines the information based on the determined physiological parameter of the patient, the information comprising an exacerbation prediction of the patient.

6. The device according to claim 5, wherein the evaluation unit is configured to evaluate the measured respiratory parameter comprising a breathing pattern or rhythm, an exhalation and/or inhalation time, a breathing volume, a dynamic flow measurement, a breathing or maximal lung capacity, and/or a breathing pulse, over a predefined time and/or at predefined intervals to determine the physiological parameter.

7. The device-according to claim 5, wherein the evaluation unit is configured to determine the flow rate and/or the flow volume of a medical gas and/or a change thereof provided in the channel, over a predefined time and/or at predefined intervals, wherein the control unit determines the information based on the determined flow rate and/or the flow volume of the medical gas.

8. The device according to claim 4, wherein the control unit is configured to be in communication with a pressure regulator of the medical gas source and/or of the patient interface to automatically adjust the medical gas flow based on the determined information and/or on a comparison of the determined information with a prescribed treatment of the patient provided in the control unit.

9. A method for determining information relating to an adherence of a patient having a respiratory disorder using a device, comprising the steps of:
   measuring a value of a first flow parameter in a fluid channel of the device, said fluid channel being configured to be in fluid communication with a medical gas source at a first end and with a patient interface at a second end, using a first sensor of a sensor arrangement of the device;
   measuring a value of a second flow parameter in said channel using a second sensor of said sensor arrangement;
   determining a flow direction of a medical gas in the channel using a control unit of the device based on the measured first flow parameter and second flow parameter communicated to said control unit; and
   determining the information using the control unit based on the determined flow direction, wherein the first sensor and the second sensor are spaced apart from each other along a longitudinal axis of the channel and are arranged at opposing ends of the channel, wherein the device is configured such that either end of the channel is configured to be coupled to the medical gas source or the patient interface, and further comprising the steps of indicating a coupling orientation of the device as part of the determined information and selecting, using the control unit, a particular sensor based on the coupling orientation and the relative position of the particular sensor to perform a measurement of a flow characteristic at a downstream end of the channel.

10. The method according to claim 9, further comprising the steps of:
   calculating a differential pressure from the measurements of the first sensor and the second sensor, wherein the first flow parameter and the second flow parameter are the same, or measuring a differential pressure, wherein one of the sensors is configured as a differential pressure sensor; and
   determining the flow direction based on the determined differential pressure, and outputting a visual and/or an acoustic alarm based on the determined information.

* * * * *